United States Patent
Kawabe et al.

(10) Patent No.: US 7,223,884 B2
(45) Date of Patent: May 29, 2007

(54) PROCESS FOR PRODUCTION OF METHIONINE

(75) Inventors: Toru Kawabe, Niigata (JP); Toshimichi Okubo, Niigata (JP); Tadashi Umezawa, Niigata (JP); Masayuki Sato, Niigata (JP); Takeomi Koga, Niigata (JP)

(73) Assignee: Nippon Soda Co., Ltd., Tokyo (JP)

( * ) Notice: Subject to any disclaimer, the term of this patent is extended or adjusted under 35 U.S.C. 154(b) by 472 days.

(21) Appl. No.: 10/493,802

(22) PCT Filed: Nov. 28, 2002

(86) PCT No.: PCT/JP02/12425

§ 371 (c)(1), (2), (4) Date: Apr. 27, 2004

(87) PCT Pub. No.: WO03/045904

PCT Pub. Date: Jun. 5, 2003

(65) Prior Publication Data

US 2004/0267049 A1    Dec. 30, 2004

(30) Foreign Application Priority Data

Nov. 29, 2001  (JP) .............. 2001-364238
Nov. 29, 2001  (JP) .............. 2001-364239

(51) Int. Cl.
    *C07C 321/00*    (2006.01)
(52) U.S. Cl. .................................... 562/559
(58) Field of Classification Search ......... 562/559
    See application file for complete search history.

(56) References Cited

U.S. PATENT DOCUMENTS 4,069,251 A    1/1978    Mannsfeld et al.
5,945,563 A *  8/1999    Imi et al. ............. 562/559

FOREIGN PATENT DOCUMENTS

| EP | 0 839 804 | 5/1998 |
|----|-----------|--------|
| JP | 04-169570 | 6/1992 |
| JP | 05-286926 | 11/1993 |

OTHER PUBLICATIONS

Supplementary European Search Report for EP 02785961.0-2103.

* cited by examiner

*Primary Examiner*—J. Parsa
(74) *Attorney, Agent, or Firm*—LaHive & Cockfield, LLP; Anthony A. Laurentano; Danielle L. Herritt

(57) ABSTRACT

A process by which high-quality crystals of methionine in the form of granules or thick plates having high bulk density can be stably produced. The process for production of methionine comprises the step of hydrolyzing 5-(2-methylmercaptoethyl)hydantoin into a metal salt of methionine by the use of at least one metal compound selected from the group consisting of metal hydroxides, metal carbonates, and metal bicarbonates, the step of neutralizing the metal salt of methionine under pressurizing with carbon dioxide to crystallize methionine, the step of separating the resulting mixture into methionine and a filtrate, and the step of recycling the filtrate to the step of hydrolysis of 5-(2-methylmercaptoethyl)-hydantoin, wherein the content of methionine polymers and/or salts thereof in the aqueous solution used in the crystallization step in terms of methionine polymers is adjusted to 8 wt % or below based on the amount of methionine to be formed.

5 Claims, 2 Drawing Sheets

PROCESS FOR PRODUCTION OF METHIONINE

FIELD OF INVENTION

The present invention relates to a process for the preparation of methionine useful as an additive for animal feed. In more detail, it relates to a process for producing bulky, high-quality crystalline methionine when 5-(2-methylmercaptoethyl)hydantoin is hydrolyzed and methionine is crystallized using carbon dioxide gas.

BACKGROUND ART

According to the descriptions on Page 129, Volume 9 of the Comprehensive Dictionary of Chemistry (published by Kyoritsu Shuppan Co., Ltd.), it is generally often the case that methionine crystals produced by neutralizing a methionine metal salt with an acid are in the shape of scales. Problems have been that such scaly crystals are extremely fragile and difficult to separate from liquids and the obtained crystals have low bulk density. To solve these problems, various methods have been proposed for changing the crystal habits by crystallizing methionine in the co-presence of additives. The following methods, for example, are known: methionine is crystallized in the co-presence of a soluble cellulose derivative (Japanese Patent No. Sho 43-22285); methionine is crystallized in the co-presence of alcohols, phenols and ketones (Japanese Patent No. Sho 43-24890); and metlionine is crystallized from a solution with an anionic or nonionic surface active agent added (Japanese Patent No. Sho 46-19610). Particularly with regard to the process for the preparation of methionine by crystallizing the compound from a methionine metal salt under the pressure of carbon dioxide gas, known methods include that methionine is crystallized in the co-presence of polyvinyl alcohol when an aqueous solution of methionine potassium salt is neutralized by absorbing carbon dioxide gas (Japanese Patent No. 2921097); methionine is crystallized in the co-presence of casein or a water-soluble polymer of semi-synthesized cellulose when an aqueous solution of methionine potassium salt is neutralized by absorbing carbon dioxide gas (Japanese Patent Laid-open No. Hei 4-244056); and methionine is crystallized in the co-presence of gluten when an aqueous solution of methionine alkali salt is neutralized with an acid (Japanese Patent Laid-open No. Hei 10-306071). If one of the above methods is however applied to a process for producing methionine by that 5-(2-methylmercaptoethyl)hydantoin is produced from a reaction solution consisting of 3-methylmercaptopropione aldehyde, hydrocyanic acid, ammonia and carbon dioxide gas and then hydrolyzed with at least one metal compound selected from the group consisting of metal hydroxides, metal carbonates and metal bicarbonates and the obtained methionine and/or its metal salt is treated to crystallize methionine with one of the above-mentioned additives under the pressure of carbon dioxide gas, crystals can be obtained in the form of granules or thick plates. In some cases, however, the obtained crystals are hollow in the inside so as to have low bulk density and have a high moisture content. Such crystals contain the mother liquor in the inside even after the crystals are separated from the liquid and washed. As a result, a large amount of inorganic salts that are originated from the mother liquor and contained in the crystals after crystals are dried is mixed in the final product of methionine, which results in a quality problem.

It is an object of the present invention to provide a process for stably producing high-quality methionine crystals in the form of granules or thick plates with high bulk density.

DISCLOSURE OF THE INVENTION

The inventors studied in earnest to achieve the above object. As a result, they found that methionine oligomer impurities produced in the step of hydrolyzing 5-(2-methylmercaptoethyl)hydantoin that is obtained from a reaction solution consisting of 3-methylmercaptopropione aldehyde, hydrocyanic acid, ammonia and carbon dioxide gas affect the form of the crystals deposited in the crystallization step using carbon dioxide gas, and that control of the content of these impurities improves the crystal form. Thus, the present invention has been completed.

The present invention relates to a process for producing methionine, characterized in that, in a process for the preparation of methionine that contains a step of hydrolyzing 5-(2-methylmercaptoethyl)hydantoin (hereinafter may be abbreviated as MHD) with at least one metal compound selected from the group consisting of metal hydroxides, metal carbonates and metal bicarbonates to give a methionine metal salt, a step of neutralizing the methionine metal salt under the pressure of carbon dioxide gas to crystallize methionine, a step of separating the resulting mixture into methionine and a filtrate and a step of recycling the filtrate for the hydrolysis of 5-(2-methylmercaptoethyl)hydantoin, the content of methionine oligomers and/or their metal salts in the aqueous solution used in the crystallization step is adjusted to 8% by weight or below, in terms of methionine oligomers, based on the amount of methionine produced.

In the MHD hydrolysis step, the hydrolysis reaction solution contains methionine oligomers and/or their metal salts in addition to a methionine metal salt. In this case, the term "methionine oligomers" refers to a group of compounds that are considered to be produced by two or more methionine molecules involved. Several structures are possible for the methionine oligomers. Among them, the compound represented by Formula (I) or (II), which is regarded to be formed by two molecules of methionine, is considered to give great influence on the crystalline form of methionine produced. The compounds of Formulae (I) and (II) are contained each alone or both of them together in the solution. They may be contained together with other compounds that fall under the definition of the said methionine oligomers other than those of Formula (I) and (II). That the methionine oligomers include the compounds of Formulae (I) and (II) refers to that they also cover methionine oligomers composed of the compound of Formula (I) or (II) each alone or only a mixture of the compounds of Formulae (I) and (II).

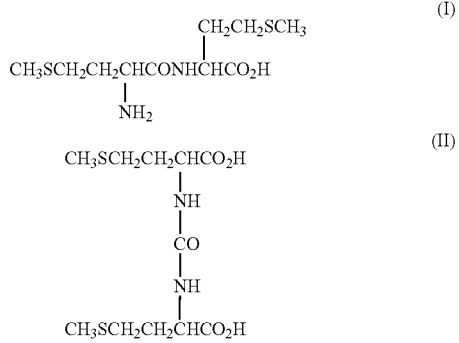

Any method can be used to control the content of methionine oligomers and/or their metal salts. The most effective way is that, because a filtrate that is recycled for the hydrolysis contains the polymers, the filtrate is treated to decompose the polymers to methionine from the viewpoint of preventing the polymers from accumulating. An actual method is that at least one metal compound selected from the group consisting of metal hydroxides, metal carbonates and metal bicarbonates is added to the filtrate, followed by heating. The filtrate is heated at a temperature of 150 to 200° C., preferably 160 to 200° C., for 0.2 to 8 hours, favorably 1 to 5 hours. It is also effective to purge part of the filtrate in order to avoid increasing an amount of impurities, such as coloring components.

Other methods to control the content of the polymers include (1) raising the reaction temperature of the hydrolysis step, (2) lengthening the reaction time, and (3) increasing a molar ratio of a metal compound to MHD. These are combined with the said heating treatment for actual implementation.

MHD can be produced by any process. It is prepared, for example, from a reaction solution consisting of 3-methylmercaptopropione aldehyde, hydrocyanic acid, ammonia and carbon dioxide gas according to a method known by those in the art It is possible to use ammonium hydrogen carbonate in place of ammonia and carbon dioxide gas.

The said process is usually carried out under the reaction conditions of pressure of about 0 to 0.3 MPa and temperature of about 70 to 110° C. From the viewpoint of recycling resources, ammonia and carbon dioxide that are generated in the next step of producing a methionine metal salt by hydrolyzing MHD may sometimes be collected to recycle in the process as ammonia and carbon dioxide or ammonium hydrogen carbonate.

A methionine metal salt is produced by hydrolysis of 5-(2-methylmercaptoethyl)hydantoin with at least one metal compound selected from the group consisting of metal hydroxides, metal carbonates and metal bicarbonates according to a known method. The hydrolysis is usually carried out at a pressure of about 0.4 to 1.0 MPa and temperature of about 140 to 200° C. for approximately 10 to 120 minutes. The reaction can be conducted by any of continuous, semi-batch and batch systems. Ammonia and carbon dioxide gas that are generated at the hydrolysis are collected and recycled to the step of MHD production. After the hydrolysis, methionine is crystallized under the pressure of carbon dioxide gas. A metal carbonate is regenerated in the filtrate after methionine is separated by filtration, and the filtrate is reused for the hydrolysis.

There are no particular restrictions on metal hydroxides, metal carbonates and metal bicarbonates that are used for the hydrolysis. Actual examples include sodium hydroxide, potassium hydroxide, sodium carbonate, potassium carbonate, sodium hydrogen carbonate and potassium hydrogen carbonate.

The content of methionine oligomers and/or their metal salts in a solution containing a methionine metal salt produced by hydrolysis is 8% by weight or below, preferably 6.5% by weight or less, in terms of methionine oligomers finally produced by neutralization with carbon dioxide gas, based on the amount of methionine produced in the same step. In this case, methionine improved in the crystal form and bulk density is stably obtained. Methionine oligomers and/or their metal salts are favorably contained less, and may not be contained at all. If a solution contains more than 8% by weight of methionine oligomers, use of other additives described in the paragraph of Background Art does not stably give methionine of a good crystalline form.

Methionine is crystallized from a hydrolysis solution containing a methionine metal salt under the pressure of carbon dioxide gas according to a known method. Applicable crystallization methods are a continuous system, batch system and a method of simultaneously charging carbon dioxide gas, a hydrolysis solution and an additive (double jet system). It is possible to use a method having both of a batch system and a semi-continuous system that is disclosed in Japanese Patent Laid-open No. Hei 11-158140.

In the aforementioned crystallization step, it is preferable to crystallize methionine in the co-presence of an additive in order to produce crystals in the form of granules or thick plates.

Any additive can be added. Its examples include gluten, polyvinyl alcohol and methyl cellulose. An amount of additive to co-exist in an aqueous solution containing a methionine metal salt is 0.05 to 0.6% by weight, preferably 0.1 to 0.3% by weight, based on the weight of methionine produced.

A method generally used in the field may be applied to a solid-liquid separation, though any can be used. Actual examples include Buchner funnels and centrifugal separators.

Materials of reactors and other equipment that are used in the process of the present invention are, as a matter of course, favorably those with excellent corrosion resistance. For example, a preferable material used for the equipment of the hydrolysis step is stainless steel containing 16 to 35% by weight of chromium, 1.0 to 6.0% by weight of molybdenum, 1.0% by weight or less of nickel, and 0.1 to 1.0% by weight of niobium and/or 0.1 to 1.0% by weight of titanium.

The stainless steel more preferably contains 0.01 to 0.08% by weight of aluminum furthermore. Actual examples include SUS444, YUS190L and NSS447MI.

In case hydrolysis is carried out at a temperature of 160° C. or below, austenite stainless steel with a high chromium content and low carbon content, such as SUS310S and YUS270, can be used.

BEST FORM TO IMPLEMENT THE INVENTION

Figure 1:
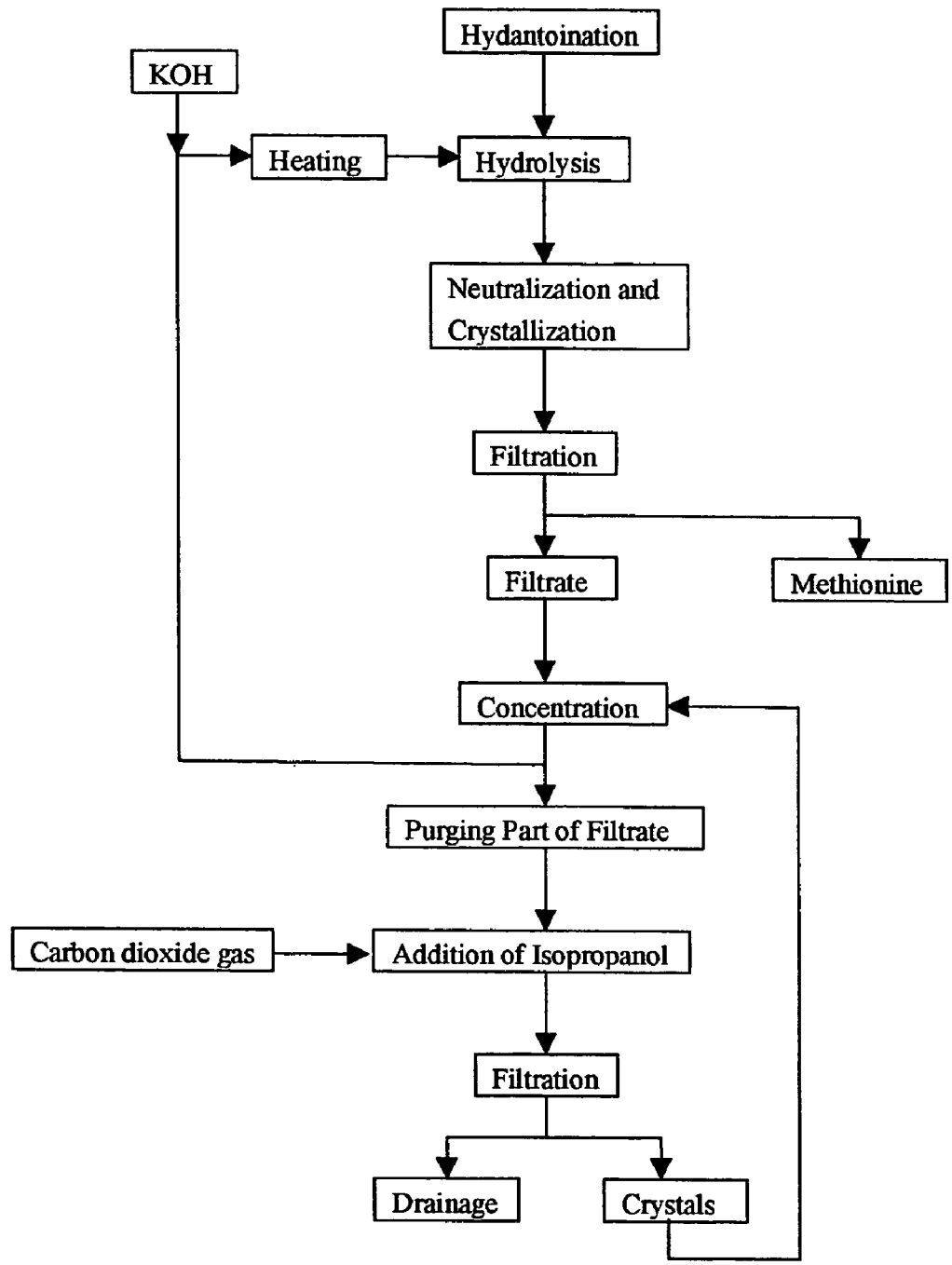
FIG. 1 shows a block flow sheet in regard to the reaction of Example 5.

The present invention is described in more detail in reference to Examples and Comparative Examples. The scope of the present invention is not however limited to the examples.

EXAMPLE 1

Into a 1800-liter reactor were simultaneously fed an aqueous solution containing 8.3% by weight of methionine, 11% by weight of potassium carbonate, 0.3% by weight of gluten based on the weight of methionine, and 4.7% by weight of the methionine dimer of Formula (I) based on the weight of methionine and 1.7% by weight of the methionine dimer of Formula (II) based on the weight of methionine, that is, 6.4% by weight of the methionine dimers based on the weight of methionine, at 1010 L/hour, and carbon dioxide gas at 20 kg/hour under pressure. The mixture was kept cooled at 15° C. with stirring, and neutralized over 1.5 hours. The resulting slurry of methionine crystals was filtrated and collected by a centrifugal separator, washed and dried to give methionine crystals. The obtained crystals contained 11.5% by weight of moisture on the wet basis, with a specific volume of 1.6 ml/g.

EXAMPLE 2

Example 1 was repeated except that 6.5% by weight of the methionine dimer of Formula (I) based on the weight of methionine and 0.9% by weight of the methionine dimer of Formula (II) based on the weight of methionine, that is, 7.4% by weight of the methionine dimers based on the weight of methionine, were used. The obtained methionine crystals contained 19% by weight of moisture on the wet basis, with a specific volume of 1.7 ml/g.

COMPARATIVE EXAMPLE 1

Example 1 was repeated except that 7.2% by weight of the methionine dimer of Formula (I) based on the weight of methionine and 1.0% by weight of the methionine dimer of Formula (II) based on the weight of methionine, that is, 8.2% by weight of the methionine dimers based on the weight of methionine, were used. The obtained methionine crystals contained 23% by weight of moisture on the wet basis, with a specific volume of 1.9 ml/g.

COMPARATIVE EXAMPLE 2

Example 1 was repeated except that 7.5% by weight of the methionine dimer of Formula (I) based on the weight of methionine and 1.5% by weight of the methionine dimer of Formula (II) based on the weight of methionine, that is, 9.0% by weight of the methionine dimers based on the weight of methionine, were used. The obtained methionine crystals contained 24% by weight of moisture on the wet basis, with a specific volume of 2.0 ml/g.

EXAMPLES 3 AND 4

In a 1-liter SUS autoclave was placed 1120 g of an aqueous solution containing 5.3% by weight of methionine, 13.0% of potassium, 1.1% by weight of the methionine dimer of Formula (I) and 0.2% of the methionine dimer of Formula (II), and further 60 g of potassium hydroxide was added. The resulting solution was heated at 150° C. and 170° C. A sample was taken with time for the calculation of a decomposition rate of each methionine dimer. HPLC was used for analyses. The decomposition rate of each methionine dimer was calculated according to the following equation. The results are shown in Table 1.

Decomposition rate (%)=[(content of a methionine dimer before heating)−(content of the methionine dimer after heating)]÷(content of the methionine dimer before heating)×100

TABLE 1

| | | Decomposition rate of methionine dimer at a reaction time | | | | | |
|---|---|---|---|---|---|---|---|
| | | 1 hour | | 2 hours | | 3 hours | |
| | Temperature | (I) | (II) | (I) | (II) | (I) | (II) |
| Example 3 | 150° C. | 27% | 75% | 43% | 87% | 57% | 100% |
| Example 4 | 170° C. | 57% | 100% | 82% | 100% | 90% | 100% |

EXAMPLE 5

According to the reaction scheme shown in FIG. 1, continuous production of methionine was carried out: 10% of the filtrate was purged, KOH was added to the filtrate to make up for the decreased amount of potassium in the filtrate due to the purging, and the filtrate was heated at 170° C. for 3 hours. A measurement of the dimer content at the hydrolysis step at the initial stage of the reaction revealed that the dimers were 7% by weight or less based on an amount of methionine produced. The obtained methionine crystals contained 12% of moisture on the wet basis, with the specific volume of 1.6 ml/g. No changes in the physical properties of the crystals were observed even after the reaction was carried out for 10 hours.

COMPARATIVE EXAMPLE 3

Figure 2:
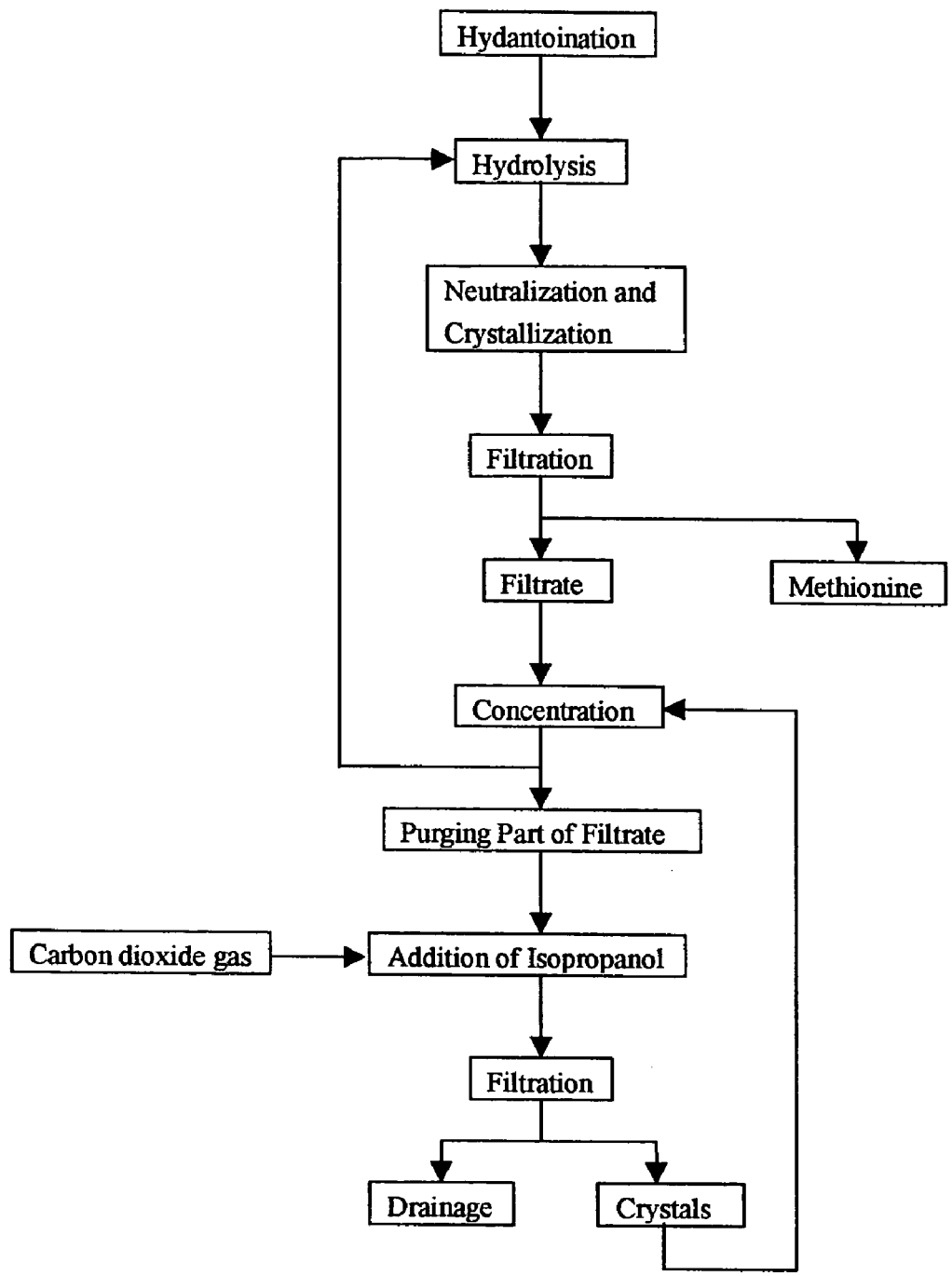
FIG. 2 shows a block flow sheet in regard to the reaction of Comparative Example 3.

Methionine was continuously produced, without adding KOH and heating the filtrate, according to the reaction process shown in FIG. 2. Methionine crystals having the same physical properties as those of the product produced in Example 5 were obtained at the initial stage of the reaction. When the reaction was carried out continuously for 10 hours, changes of the physical properties of the obtained methionine crystals were observed. Measurements showed that the moisture content was 26% on the wet basis, and the specific volume 2.0 ml/g. The amount of the methionine dimers and/or their potassium salts in the reaction solution at the hydrolysis step at that time was measured to be 9% by weight based on the weight of methionine produced.

APPLICABILITY IN INDUSTRY

As described above, use of the process of the present invention enables to produce methionine crystals that are more closely packed so as to have a smaller specific volume with a lower moisture content than those produced according to the conventional processes, while keeping the same crystal habits as before. The crystalline product greatly decreases load on dryers used in the methionine production and reduces a size of methionine package so as to cut down transport cost. Therefore the present invention is valuable in industrial applications.

What is claimed is:

1. A process for producing methionine comprising hydrolyzing 5-(2-methylmercaptoethyl) hydantoin with at least one metal compound selected from the group consisting of metal hydroxides, metal carbonates and metal bicarbonates to give a methionine metal salt, neutralizing the methionine metal salt under the pressure of carbon dioxide gas to crystallize methionine, separating the resulting mixture into methionine and a filtrate and recycling the filtrate for the hydrolysis of 5-(2-methylmercaptoethyl) hydantoin, wherein the content of methionine oligomers and/or their metal salts in the aqueous solution used in the crystallization step is adjusted to 8% by weight or below in terms of methionine oligomers based on the amount of methionine produced.

2. The process for producing methionine according to claim 1, wherein a compound represented by Formula (I)

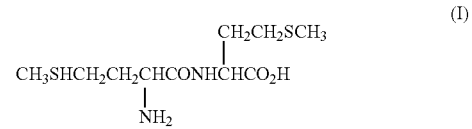

and/or a compound represented by Formula (II)

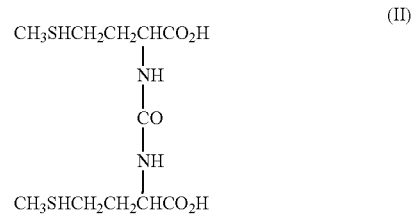

are included in the methionine oligomers.

3. The process according to claim 1 wherein the at least one metal compound selected from the group consisting of metal hydroxides, metal carbonates and metalbocarbonates is added to the filtrate in the step of recycling the filtrate and the resulting filtrate is heated.

4. The process according to claim 3, wherein the filtrate is heated in a range 150 to 200° C.

5. The process according to claim 1, wherein the metal compound is a potassium compound.

* * * * *

UNITED STATES PATENT AND TRADEMARK OFFICE
CERTIFICATE OF CORRECTION

PATENT NO. : 7,223,884 B2 Page 1 of 1
APPLICATION NO. : 10/493802
DATED : May 29, 2007
INVENTOR(S) : Toru Kawabe et al.

It is certified that error appears in the above-identified patent and that said Letters Patent is hereby corrected as shown below:

In the Claims:

In Claim 2, column 8, lines 1-20, please replace

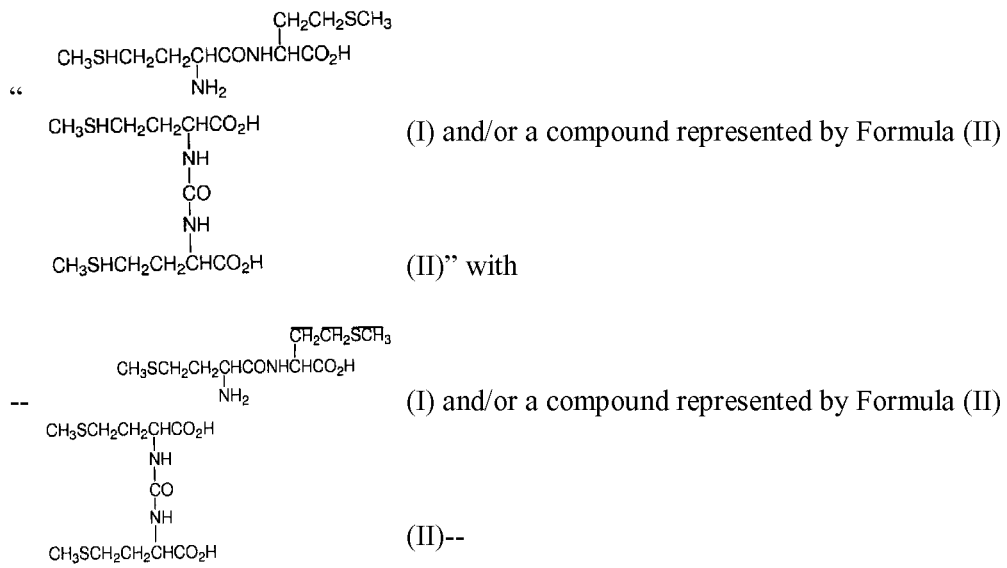

In Claim 3, column 8, line 25, please replace "metal hydroxides, metal carbonates and metalbocarbonates" with --metal hydroxides, metal carbonates and metal bicarbonates--

Signed and Sealed this

Sixth Day of May, 2008

JON W. DUDAS
*Director of the United States Patent and Trademark Office*